(12) United States Patent
Madigan et al.

(10) Patent No.: US 10,736,891 B2
(45) Date of Patent: Aug. 11, 2020

(54) COMPOSITION AND METHOD FOR TREATING CHAGAS DISEASE

(71) Applicants: Roy Madigan, Spring Beach, TX (US); Alberto Paniz-Mondolfi, Spring Beach, TX (US)

(72) Inventors: Roy Madigan, Spring Beach, TX (US); Alberto Paniz-Mondolfi, Spring Beach, TX (US)

( * ) Notice: Subject to any disclaimer, the term of this patent is extended or adjusted under 35 U.S.C. 154(b) by 348 days.

(21) Appl. No.: 14/990,031

(22) Filed: Jan. 7, 2016

(65) Prior Publication Data
US 2017/0196852 A1    Jul. 13, 2017

(51) Int. Cl.
| | |
|---|---|
| *A61K 31/496* | (2006.01) |
| *A61K 9/10* | (2006.01) |
| *A61K 9/00* | (2006.01) |
| *A61K 9/16* | (2006.01) |
| *A61K 47/44* | (2017.01) |
| *A61K 9/08* | (2006.01) |
| *A61K 31/343* | (2006.01) |

(52) U.S. Cl.
CPC .......... *A61K 31/496* (2013.01); *A61K 9/0053* (2013.01); *A61K 9/0095* (2013.01); *A61K 9/08* (2013.01); *A61K 9/10* (2013.01); *A61K 9/1623* (2013.01); *A61K 31/343* (2013.01); *A61K 47/44* (2013.01); *Y02A 50/414* (2018.01)

(58) Field of Classification Search
CPC .......... A61K 31/343; A61K 9/10; A61K 9/14; A61K 9/20; A61K 9/28; A61K 9/48; A61K 9/50
See application file for complete search history.

(56) References Cited

U.S. PATENT DOCUMENTS

| | | | |
|---|---|---|---|
| 6,039,981 | A | 3/2000 | Woo et al. |
| 2002/0183347 | A1 | 12/2002 | Meade et al. |
| 2003/0216353 | A1 | 11/2003 | Mosher et al. |
| 2013/0337138 | A1 | 12/2013 | Prukayastha et al. |

OTHER PUBLICATIONS

Benaim et al. Amiodarone has intrinsic anti-tryapnosoma cruzi activity and acts synergistically with pocasonazole. J. Med. Chem. 2006, 49, 892-899.*

Diniz et al. Benznidazole and posaconazole ion experimental chagas disease:positive interaction in concomitant and sequential treatments. PLOS Neglected tropical diseases Aug. 2013 vol. 7:(8):1-8.*
Barone et al. Food interaction and steady state pharamacokinetics of itraconazole capsules in healthy male volunteeers. Antimicrobial agents and chemotherapy. Apr. 1993:37(4):778-784.*
International Search Report dated Mar. 1, 2017 in PCT/US17/12278.
Written Opinion dated Mar. 1, 2017 in PCT/US17/12278.
Paniz-Mondolfi, et al., "Amiodarone and Itraconazole: A Rational Therapeutic Approach for the Treatment of Chronic Chagas' Disease", May 19, 2009, pp. 228-233, vol. 55, Chemotherapy 2009.
Czajkowska-Kosnik, et al., "Development and Evaluation of Liquid and Solid Self-Emulsifying Drug Delivery Systems for Atorvastatin", Nov. 25, 2015, pp. 21010-21022, vol. 20, Molecules 2015.
Mayo Clinic, "Itraconazole (Oral Route)" URL=http://www.mayoclinic.org/drugssupplements/itraconazoleoralroute/properuse/drg20071421, Jan. 1, 2016, first and second pages.
Kumar, et al., "In Vitro and In Vivo Performance of Different Sized Spray-Dried Crystalline Itraconazole", Sep. 5, 2014, pp. 3018-3021, vol. 104, Journal of Pharmaceutical Sciences.
Pfisterer, et al., "Important Differences Between Short-and Long-Term Hernodynamic Effects of Amiodarone in Patients with Chronic Ischemic Heart Disease at Rest and During Ischemia-induced Left Ventricular Dysfunction", May 1985, pp. 1205-2011, vol. 5, No. 5, JACC.
Robinson, et al., "Stability of plasma amiodarone levels during chronic oral therapy", Mar. 1990, pp. 539-530, vol. 4, issue 2, Cardiovascular Drugs and Therapy.
Mayo Clinic, "Amiodarone (Oral Route)" URL=http://www.mayoclinic/org/drugssupplements/amiodaroneoralroute/properuse/drg20061854, Jan. 1, 2016.
Hardin, et al., "Pharmacokinetics of Itraconazole following Oral Administration to Normal Volunteers", Sep. 1988, pp. 1310-1313, Antimicrobial Agents and Chemotherapy.
Apt, et al., "Treatment of Chagas' disease with itraconazole: electrocardiographic and parasitological conditions after 20 years of follow-up", May 3, 2013, pp. 2164-2169, vol. 68, J Antimicrob Chemother.

(Continued)

*Primary Examiner* — Lakshimi S Channavajjala
(74) *Attorney, Agent, or Firm* — B. Aaron Schulman, Esq.; Stites & Harbison, PLLC

(57) ABSTRACT

The presently disclosed subject matter provides a pharmaceutical composition and a method of treating Chagas disease. The pharmaceutical composition includes a dose of Itraconazole and a dose of Amiodarone and may be in the form of a liquid oral suspension. The liquid oral suspension may be produced through the use of pharmaceutically acceptable beads. In addition, the Itraconazole may be micronized to a small particle size before being formed into a composition with Amiodarone. The method for treating Chagas disease is effected by administering an effective amount of this pharmaceutical composition to a subject in need thereof, and the present composition is safer and more effective than previous compositions and with fewer undesirable side effects.

12 Claims, No Drawings

(56) References Cited

OTHER PUBLICATIONS

Tsimogianni, et al., "Cardiac arrest provoked by itraconazole and amiodarone interaction: a case report", Jul. 29, 2011, p. 2, vol. 5, No. 333, Journal of Medical Case Reports 2011.
A.E. Paniz-Mondolfi, et al., "Amiodarone and Itraconazole: a Rational Therapeutic Approach for the Treatment of Chronic Chagas' Disease", Chemotherapy, (May 19, 2009); vol. 55, pgs. 228-233.
S. Kumar, et al., "In Vitro and In Vivo Performance of Different Sized Spray-Dried Crystalline Itraconazole", Journal of Pharmaceutical Sciences, (2015); vol. 104, pp. 3018-3028.
International Preliminary Report on Patentability dated Jul. 19, 2018 in PCT/US17/012278.

\* cited by examiner

COMPOSITION AND METHOD FOR TREATING CHAGAS DISEASE

FIELD OF THE INVENTION

The presently disclosed subject matter relates to a pharmaceutical composition and method of using the composition for treating Chagas disease. More particularly, the presently disclosed subject matter relates to a pharmaceutical composition comprising a dose of Itraconazole and a dose of Amiodarone and a method of administering this pharmaceutical composition in order to treat Chagas disease patients.

BACKGROUND OF THE INVENTION

Chagas disease, also known as American trypanosomiasis, is a parasitic zoonosis resulting from the infection with the hemoflagellate protozoan *Trypanosoma cruzi*, which can be transmitted to humans by blood-sucking triatomine insects, via blood transfusions, infected organ transplantation and/or vertical transmission (Gascon et al., 2007; Punukollu et al., 2007). American trypanosomiasis is widespread in the Americas, and endemic to Central and South America. It has been detected in 18 Latin American countries, affecting up to 20 million people from Mexico to Patagonia (Urbina et al., 2003).

Chagas disease may be quickly fatal, especially in children, or it may be carried asymptomatically for decades. Clinically, Chagas disease has a short-term acute and a long-term chronic phase. The short-term acute phase has very few clinical symptoms. However, chagasic cardiomyopathy is often the most prominent feature of the long-term chronic phase, which is usually accompanied by severe gastrointestinal and/or cardiac complications which result in permanent physical disability or death. Between 10-30% of infected people eventually develop severe cardiac or digestive chronic involvement as late manifestations of Chagas disease.

Despite the growing interest in the development of new drugs for treatment, the specific therapy for Chagas disease remains unsatisfactory in the prevalent chronic stages of *Trypanosoma cruzi* infection (Urbina et al., 2003). Current treatment of the acute phase is based on only two compounds: nitrofurans (nifurtimox) and nitro-imidazoles (benznidazole). However, these drugs have proven to be of limited efficacy during the acute as well as the chronic phase, most likely due to the presence of naturally resistant strains to these drugs. Moreover, treatment based on nitroheterocyclic compounds and nitroimid-azole derivatives frequently produce deleterious side effects in the patient, thereby limiting their use (Urbina et al., 2003; Benaim et al., 2006). Previously, it has been suggested that a combination of amiodarone and itraconazole may provide a rational therapeutic approach for the treatment of chronic Chagas disease (Paniz-Mondolfi et al. 2009), but this has not led to a pharmaceutical composition which can effectively treat Chagas disease without adverse side effects. Accordingly, a more effective and safer new treatment regimen is therefore still a desired goal for the treatment of Chagas disease.

SUMMARY OF THE INVENTION

This section describes several embodiments of the presently-disclosed subject matter, and, in many cases, lists variations and permutations of these embodiments. This section is thus merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this section or not. To avoid excessive repetition, this section does not list or suggest all possible combinations of such features.

In accordance with the present invention, the presently disclosed subject matter provides a pharmaceutical composition for treating Chagas disease. The pharmaceutical composition includes a dose of Itraconazole wherein the dosage is in the range of about 0.1 mg/kg to about 50 mg/kg based on the subject receiving said treatment, and a dose of Amiodarone wherein the dosage is in the range of about 2.5 mg/kg to about 20 mg/kg based on the subject receiving said treatment. In general, the dosage should be sufficient to result in a plasma concentration in the patient of about 0.1 to 3.0 µg/ml, or in another embodiment from about 0.3 to 2.0 µg/ml. In some embodiments, the pharmaceutical composition further includes a pharmaceutically acceptable carrier. Yet further, in some embodiments, the pharmaceutical composition may also include a second pharmaceutically acceptable carrier. In some embodiments, the presently disclosed subject matter provides that the dose of Itraconazole is first mixed with the second pharmaceutically acceptable carrier.

Further provided in some embodiments of the presently disclosed subject matter, is a liquid oral suspension of a pharmaceutical composition for treating Chagas disease. The pharmaceutical composition includes a mixture of a dose of Itraconazole and a dose of Amiodarone suspended in a first pharmaceutically acceptable carrier. In some embodiments, the composition further includes a second pharmaceutically acceptable carrier. In some embodiments, the presently disclosed subject matter provides that the dose of Itraconazole is mixed with the second pharmaceutically acceptable carrier.

In some embodiments, the presently disclosed subject matter provides a method of treating Chagas disease in a subject in need thereof. The method comprises administering to the subject a pharmaceutical composition comprising a dose of Itraconazole wherein the dose of Itraconazole is in the range of about 0.1 mg/kg to about 50 mg/kg, and a dose of Amiodarone wherein the dose of Amiodarone is in the range of about 2.5 mg/kg to about 20 mg/kg. In additional embodiments, the Itraconazole is micronized or nanomilled to a small particle size of about 1 to 400 nm.

Still further provided in accordance with the presently disclosed subject matter is a method of producing an oral suspension of a pharmaceutical composition. The method includes the steps of (a) applying a dose of Itraconazole to a pharmaceutically acceptable beads, (b) admixing the mixture of step (a) to a dose of Amiodarone, wherein the Amiodarone is in a powdered form, and (c) suspending the mixture of step (b) in a pharmaceutically acceptable carrier. In some embodiments, the method further comprises the step of adding a flavor enhancer.

Advantages of the presently-disclosed subject matter will become evident to those of ordinary skill in the art after a study of the description, and non-limiting Examples as set forth herein.

DESCRIPTION OF EXEMPLARY EMBODIMENTS

The details of one or more exemplary non-limiting embodiments of the presently-disclosed subject matter are set forth herein. Modifications to embodiments described herein and other embodiments will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. While the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although a number of methods, devices, and materials similar or equivalent to those described herein may be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a subject" includes a plurality of such subjects, and so forth.

Unless otherwise indicated, all numbers expressing quantities of ingredients, properties such as reaction conditions, and so forth used in the specification and claims are to be understood as being modified in all instances by the term "about."

Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently disclosed subject matter relates to a pharmaceutical composition for treating Chagas disease, methods of treatment thereof, and methods of producing the composition thereof. More particularly, the presently disclosed subject matter relates to a composition comprising a dose of Itraconazole and a dose of Amiodarone and a method of using this composition for the treatment of Chagas disease.

In some embodiments, the presently disclosed subject matter provides a pharmaceutical composition for treating Chagas disease. In an exemplary embodiment, the pharmaceutical composition includes a dose of Itraconazole wherein the dose of Itraconazole is in the range of about 0.1 mg/kg to about 50 mg/kg, and a dose of Amiodarone wherein the dose of Amiodarone is in the range of about 2.5 mg/kg to about 20 mg/kg. In one specific embodiment, the dose of Itraconazole is about 10 mg/kg and the dose of the Amiodarone is about 7.5 mg/kg. In some embodiments, the Itraconazole and Amiodarone can be administered separately. In general, the dosage should be sufficient to result in a plasma concentration in the patient of about 0.1 to 3.0 μg/ml, or in another embodiment, from about 0.3 to 2.0 μg/ml.

Amiodarone is an antiarrhythmic agent used for various types of cardiac dysrhythmias, both ventricular and atrial. As a versatile anti-arrhythmic agent, Amiodarone is frequently prescribed to patients due to the presence of complex arrhythmias in Chagas' cardiomyopathy (Gascon et al., 2007). In specific instances, Amiodarone is used not only to control the patient's arrhythmogenic status, but also to challenge the recently described anti-$T.$ $cruzi$ activity of this drug (Benaim et al., 2006). Amiodarone appears to have a combined mechanism of action by disrupting the parasites' calcium ($Ca^{2+}$) homeostasis and also by interfering with the sterol biosynthesis of the parasite's membrane in both proliferative stages of $T.$ $cruzi$, including the clinically relevant intracellular amastigote form of the parasite (Benaim et al., 2006). This drug increases the release of $Ca^{2+}$ from intracellular compartments and also induces a rapid release of $Ca^{2+}$ from the parasite's mitochondria causing a collapse of its membrane potential due to the increase of cytoplasmic $Ca^{2+}$ (Benaim et al., 2006). On the other hand, experimental results indicate that amiodarone inhibits de novo sterol synthesis at a prelanosterol level, probably due to the known properties of $Ca^{2+}$ channel blockers which inhibit sterol isomerases (Benaim et al., 2006; Krajewska-Kulak et at, 1993; Moebius et al., 1998), in a similar fashion to other imidazoles and sterol analogs (Urbina et al., 1996).

As used herein, in some embodiments, the present subject matter provides a pharmaceutical composition containing a daily dose of Amiodarone in the range of about 2.5 mg/kg to about 20 mg/kg. In specific embodiments, the daily dose of Amiodarone can be any dosage between about 2.5. and 20 mg/kg, e.g., dosages in every 0.5 mg/kg interval, namely about 2.5 mg/kg, about 3.0 mg/kg, about 3.5 mg/kg, and so forth up to about 20.0 mg/kg. For example, the daily dose of Amiodarone may be about 7.5. mg/kg.

Itraconazole is a synthetic imidazole-triazole derivative prescribed to patients with fungal infections. Itraconazole may be given orally or intravenously. In some embodiments of the presently disclosed subject matter, Itraconazole is initiated in an effort to obtain a synergistic effect in association with amiodarone. As it has been described, $T.$ $cruzi$ shares with fungi the need for ergosterol in order to maintain cell viability and proliferation (Urbina et al., 2003; Urbina et al., 2002). Inhibition of ergosterol synthesis using triazoles has proven to be effective against $T.$ $cruzi$, acting through cytochrome P-450-dependent C14 sterol demethylase inhibition leading to accumulation, which is toxic for many membrane-bound enzyme systems including the electron transport system (Urbina et al., 2001; Molina et al., 2000; Urbina et al., 1998). Previous study shows that, after 2 months of using itraconazole treatment, anti-rTc24 titers of a patient dropped even more, reaching levels beneath the cut off points by the 6th month with persistently positive immunofluorescence, indicating that the patient became dissociated and parasitologically cured as confirmed by complement-mediated lysis with notable clinical improvement. (Paniz-Mondolfi, et al., 2009).

As used herein, in some embodiments, the presently disclosed subject matter provides a pharmaceutical composition containing a daily dose of Itraconazole in the range of about 0.1 mg/kg to about 50 mg/kg. In specific embodiments, the daily dose of Itraconazole can dosage between about 0.1 and 50.0 mg/kg, e.g., dosages in every 0.5 mg/kg interval, namely about 0.5 mg/kg, about 1.0 mg/kg, about 1.5 mg/kg, and so forth up to about 50.0 mg/kg, For example, the daily dose of Itraconazole may be about 1.0 mg/kg.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In some embodiments, the associated disease is Chagas disease.

In some embodiments, the pharmaceutical composition further includes a pharmaceutically acceptable carrier. In some embodiments, the pharmaceutical composition is suspended in the pharmaceutically acceptable carrier. A non-limiting example of the first pharmaceutically acceptable carrier is an oily solvent medium. As would be recognized by one of ordinary skill in the art, the oily solvent medium can be any pharmaceutically acceptable oil suitable to act as a suitable solvent for the active ingredients. The oily solvent medium can be a vegetable oil or a nut oil, with one non-limiting example of the oily solvent medium being almond oil.

As used herein, the term "pharmaceutical carrier" or "pharmaceutically acceptable carrier" may refer to any of a wide variety of materials known for general usage in delivering a pharmaceutical agent or agents to a patient. Non-limiting examples of such carriers include sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The form of the present composition may be a suspension as disclosed herein, but may take on other suitable forms including a capsule, tablet, caplet, or any other convention form for administering pharmaceutical compounds and compositions. Administration can be in a number of suitable ways including oral administration.

Further provided, in some embodiments of the presently disclosed subject matter, is a second pharmaceutically acceptable carrier. In some embodiments, the dose of Itraconazole is mixed with the second pharmaceutically acceptable carrier. One non-limiting example of the second pharmaceutically acceptable carrier is lactose.

Further still, in some embodiments, the presently disclosed subject matter provides that the pharmaceutical composition further contains a flavor enhancer which may be a fruit-flavored enhancer. Non-limiting examples of the flavor enhancer is *stevia* and banana. In some embodiments of the presently disclosed subject matter, the pharmaceutical composition is adapted for a once-daily oral dosing.

Suitable formulations of the present composition may include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain form ulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by a number of conventional methods well known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The composition can also be formulated as a preparation for implantation or injection. Thus, for example, the compounds can be formulated with suitable polymeric or hydrophobic materials (e.g., as an emulsion in an acceptable oil)

or ion exchange resins, or as sparingly soluble derivatives (e.g., as a sparingly soluble salt).

The composition can also be formulated in rectal compositions (e.g., suppositories or retention enemas containing conventional suppository bases such as cocoa butter or other glycerides), creams or lotions, or transdermal patches.

In some embodiments of the presently disclosed subject matter, a liquid oral suspension for treating Chagas disease is provided. The liquid oral suspension contains a mixture of a dose of Itraconazole and a dose of Amiodarone suspended in a pharmaceutically acceptable carrier. A non-limiting example of the pharmaceutically acceptable carrier is an oily solvent medium such as almond oil.

In some embodiments, the liquid oral suspension of the disclosure may further contain a second pharmaceutically acceptable carrier, and the Itraconazole is mixed with the second pharmaceutically acceptable carrier. A non-limiting example of the second pharmaceutically acceptable carrier is lactose.

Further provided, in some embodiments of the presently disclosed invention, is a liquid oral suspension that contains the Itraconazole in an amount within the range of about 0.5 to 3 weight % based on the total weight of the suspension, and in some embodiments, the suspension contains Amiodarone in an amount within the range of about 1 to 3 weight % based on the total weight of the suspension. Further, in some embodiments, the weight percent of Itraconazole in the suspension may be about 2.5%, and the weight percent of Amiodarone may be about 2.0% based on the total weight of the suspension. In some embodiments, such as where the Itraconazole has been micronized, the liquid oral suspension may contain Itraconazole in an amount of about 1% by weight of the total weight of the suspension. The suspension of the present invention may contain an amount of Itraconazole suitable to attain a blood concentration of Itraconazole in the range of from about 0.1 µg/mL to about 3.0 µg/mL, or in another embodiment, from about 0.3 µg/ml to about 2.0 µg/ml. In additional embodiment, the Itraconazole therapeutic efficacy may be maximized when serum concentrations exceed 0.5 mcg/mL for localized infections, or 1.0 mcg/mL for systemic infections.

In some embodiments, the liquid oral suspension further contains a flavor enhancer. The flavor enhancer can be added to the liquid oral suspension to achieve a good tasting product. Flavor enhancers provide a more pleasant sensation in the subject's mouth during consumption of the liquid oral suspension. Non-limiting flavor enhancers are stevia and banana, but numerous other flavors, including fruit flavors such as strawberry, raspberry, cherry, grape, or other flavors commonly used to enhance pharmaceutical compounds and compositions may be utilized.

In one embodiment of the presently disclosed invention, the itraconazole may be prepared as a formulation through a process of micronization or nanomilling. Such a process is useful in order to increase bioavailability of itraconazole by 2000% or greater, for example by reducing the particle size of itraconazole to between 1 and 400 nm, e.g., around 240-280 nm, or 260 nm. In such a process, the itraconazole can be spray dried onto a suitable carrier such as a sugar molecule (e.g., lactose or mannitol) and given orally. Such a micronization process allows for minimizing the amount of the drug provided to patients with the same therapeutic effect. For example, compared to the non-micronized version, the micronized version allows for the compositions of the present invention to use roughly 1/20 of the drug in the pharmaceutical composition, and this will substantially reduce manufacturing costs and be able to substantially reduce the cost of treatment to the patient. essentially save our target population a significant amount of expense. This is particularly important considered that there is an estimated 11-20 million people with Chagas disease in Central and South America where a large percentage of patients are impoverished.

In one embodiment of preparing the itraconazole in accordance with the present invention, the itraconazole can be nanometrically milled using conventional wet milling equipment well known in the art. For example, a suspension of itraconazole may be prepared and then subject to milling using a media mill such as disclosed in Kumar et al., J. Pharm. Sci. 104:3018-3028 (2015), incorporated herein by reference. In one suitable process, itraconazole (1%, w/v) can be suspended in a desired concentration of an aqueous stabilizer solution, and the prepared suspension can be stirred for 30 minutes or more for complete wetting of the drug by the stabilizer solution. The suspension (e.g., 150 mL) may then be wet milled or wet grinded using a conventional wet milling or grinding device such as a media mill, for example, such as those manufactured by Netzsch of Exton, Pa. Using this equipment, the mill may be operated at a suitable speed, e.g., 2500 rpm in a continuous mode for a time suitable to reduce particle size to a range of 1 and 400 nm, e.g., 75 minutes. The temperature of the sample can be maintained at below 25° C. during the process, and as needed, two cooling bath recirculators may be used, including one attached to the milling device and the other attached to suspension recirculation chambers.

After the milling process, the nano- and microcrystalline suspensions of itraconazole may be spray dried onto a suitable substrate, such as a sugar molecule (e.g., lactose or mannitol) using a conventional spray drying apparatus such as a B-290 spray drier manufactured by Buchi Labortechnik AG of Flawil, Switzerland. In the spray drying process, the drier is set at a suitable temperature, e.g. 75° C. for the outlet and 110° C. for the inlet. As indicated above, the spray drying using a suitable excipient, e.g., lactose or mannitol, which is useful in preventing against nanocrystal aggregation. The spray-dried powders resulting from this process contain itraconazole at a reduced particle size, e.g., 1-400 nm, and these powders can be used in accordance with the present invention.

The presently disclosed subject matter further provides a method of treating Chagas disease in a subject in need thereof. The method includes administering to the subject in need thereof a dose of Itraconazole wherein the dose of Itraconazole is in the range of about 0.1 mg/kg to about 50 mg/kg and a dose of Amiodarone wherein the dose of Amiodarone is in the range of about 2.5 mg/kg to about 20 mg/kg. In some embodiments, the Itraconazole and Amiodarone are administered in the form of a pharmaceutical composition, and in other embodiments, the Itraconazole and Amiodarone are administered separately. In additional embodiment, the subject is a mammal, such as a human, dog, or monkey. In some embodiments, the Itraconazole and Amiodarone are administered once daily, and in other embodiment, they may be taken in conjunction with a meal or food.

In some embodiments, the presently disclosed subject matter provides a method of treating Chagas disease in a subject in need thereof. The method includes administering to the subject a liquid oral suspension of Itraconazole and Amiodarone. The liquid oral suspension may contain a mixture of a dose of Itraconazole and a dose of Amiodarone suspended in a pharmaceutically acceptable carrier. In some embodiments, the subject is a human, but may also be a dog or monkey. In some embodiments, the suspension is administered once daily. In some embodiments, the suspension is taken in conjunction with a meal.

Further provided, in some embodiments of the presently disclosed subject matter, is a method of producing an oral suspension containing the pharmaceutical composition of the disclosure. The method may include the steps of (a) applying a dose of Itraconazole to a pharmaceutically acceptable beads, (b) admixing the beads of step (a) with a dose of Amiodarone, wherein the Amiodarone is in a powdered form, and (c) suspending the mixture of step (b) in a pharmaceutically acceptable carrier. In some embodiments, the method further includes the step of adding a flavor enhancer, and in other embodiments, the pharmaceutically acceptable beads are sugar beads. In other embodiments, the method includes micronizing or nano-milling the Itraconazole to a particle size of about 1 to 400 nm. The pharmaceutically acceptable carrier may also be an oily solvent medium.

In some embodiments, the method provides that the dose of Itraconazole in the suspension is in the range of about 0.1 mg/kg to about 50 mg/kg, and is given once daily. In some embodiments, the total daily dosage is about 10 mg/kg per day. In some embodiments, the method provides that the dose of Amiodarone is in the range of about 2.5 mg/kg to about 20 mg/kg, and is given once daily. In some embodiment, the total daily dosage is about 7.5 mg/kg per day. In some embodiments, the dosages of Itraconazole and Amiodarone are given at the same time, whether sequentially or together in a single composition, e.g., suspension or capsule, and in other embodiments, they can be administered separate times of the day (e.g., 12 hours apart), but overall can be administered together every 24 hours. The dosages are also preferably administered with food, and may be administered orally.

The term "administering" refers to any method of providing a compound and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition (e.g., Chagas disease). In further various aspects, a preparation can be administered prophylactically; that is, administered for prevention of a disease or condition.

In some embodiments, a subject will be administered an effective amount of the pharmaceutical composition. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Accordingly, the presently disclosed subject matter provides a method of treating Chagas disease comprising administering to a subject in need thereof an effective amount of a dose of Itraconazole and a dose of Amiodarone. The Itraconazole and Amiodarone may be administered separately or simultaneously such as in the form of a pharmaceutical composition. The pharmaceutical composition may be in the form of a suspension and may include a suitable pharmaceutical carrier such as an oily solvent medium.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, dog, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The presently-disclosed subject matter is further illustrated by the following specific but non-limiting examples. Some of the following examples are prophetic, notwithstanding the numerical values, results and/or data referred to and contained in the examples.

EXAMPLES

The examples below refer to treatment regimens for Chagas' disease using a combination of Itraconazole and Amiodarone in accordance with the present invention.

Example 1

In this study, Itraconazole and Amiodarone are formulated into one pharmaceutical composition in the form of an oral suspension.
Methods of Treatment
A daily dose of the oral suspension contains Itraconazole at about 10 mg/kg once daily and Amiodarone at about 7.5 mg/kg once daily. In making this oral suspension composition, Itraconazole is first infused to lactose "sugar" beads, and mixed with a pure powdered form of Amiodarone. Then the mixture of Itraconazole and Amiodarone was suspend in an almond oil base, flavored with *stevia* and/or banana. The pharmaceutical composition was taken with a meal by patients suffering from Chagas' disease. The oral suspension was administered once daily for 6 months with strict monitoring of hepatic, renal and cardiovascular function.

Diagnosis and Follow-Up

Following administration to patients, serologic assays of the patient were performed using three novel, highly specific and sensitive recombinant proteins of *T. cruzi*, by both ELISA and immunoblotting, to diagnose Chagas' disease. To evaluate the effectiveness of the treatment, clinical evolution and follow-up of the patient was complemented with a bimonthly determination of anti-rTc24 (PGR24-His) antibody (lytic antibodies) levels by ELISA and immunoblot. Additionally, indirect immunofluorescence (IIF) and complement-mediated lysis (CML) were performed as described below.

ELISA Testing

Microtiter plaque (High Binding, Costar, Cambridge, Mass., USA) was sensitized overnight at 4° C. with 100 l of 0.5 M carbonate-bicarbonate buffer (pH 9.6) containing 20 ng of each recombinant antigen per well (PGR31-His, PGR30-His and rTc24-His) or rTc24 (PGR24-His) alone for the follow-up assays (Laboratorio de Enzimologia de Pardsitos, Merida, Venezuela). After 5 washes with 0.15 M phosphate-buffered saline (PBS, pH 7.2) containing 0.05% of Tween 20 (Sigma Chemical Co., St. Louis, Mo., USA; PBS-Tween 20) wells were blocked for 1 h at 37° C. with 200 μl of 5% nonfat milk in PBS-Tween 20. After washing 5 times with PBS-Tween 20, the plaque was incubated for 1 h at 37° C. with 10 μl of the patient's serum diluted 1:100 in PBS-Tween 20 solution plus 1% nonfat milk. After rinsing 5 times with PBS-Tween 20, the plaque was incubated for 1 h at 37° C. with peroxidase-labeled secondary antibody anti-human IgG (-chain-specific, Sigma Chemical Co.). The plaque was then washed 5 times and 100 μl of 0.2% 3'3'5'5'-tetramethylbenzidine plus 0.1% hydrogen peroxide (Sigma Chemical Co.) was added to each well followed by incubation at 37° C. for 15 min. Reactions were stopped by adding 50 μl/well of a 20% sulfuric acid solution and optical densities were determined at 405 nm using an automated ELISA reader (Multi-skan Ascent, Thermo Electron). AH assays were performed in triplicate.

Transference of the antigens to the nitrocellulose membrane (0.45 μm, Hybond, Amersham Biosciences, GE) was performed by incubating for 3 h at room temperature (RT) 60 μl of 0.05 M carbonate-bicarbonate buffer pH 9.6 containing 500 ng of each recombinant antigen (PGR31-His, PGR30-His and PGR24-His, or rTC24 alone in follow-up assays) in parallel lines, using a Mini-blotter 28 SL (Immunogenetics, Cambridge, Mass., USA).

After blocking (5% nonfat milk in PBS plus 0.1% Tween 20) for 1 h at RT and washing with PBS, the membrane was air-dried and then cut into strips (width: 4 mm, length: 2 cm). The strips were incubated for 1 h at 37° C. with gentle shaking in independent channels (Mini Incubation Tray, BioRad) with 10 μl of the patient's serum diluted 1:100 with 1% nonfat milk in PBS-Tween 20. The strips were then washed 5 times with PBS-Tween 20 and incubated for 1 h at 37° C. with gentle shaking with 1 ml of a per-oxidase-labeled secondary antibody anti-human IgG (-chain-specific, Sigma Chemical Co.) dilution (1:5,000), Following 5 washes with PBS-Tween 20, 1 ml of a 3,3'-diaminobenzidine solution containing 0.1% of hydrogen peroxide (Sigma Chemical Co.) was added to each channel; color development was allowed to proceed by incubating the strips with this solution for 10 min at RT. Finally, the strips were washed and air-dried to proceed with the visual reading of the results, where the patient's serum was considered to be 'positive' in the diagnosis assays if at least 2 antigen bands were visualized.

For the follow-up assays, the patient was considered cured if anti-rTc24 antibodies levels were below the cut-off by ELISA and recognition of the rTc24 antigen by immunoblot was identical to the negative control, i.e. no detectable reactivity with the antigen.

$1\times10^7$ African green monkey kidney cells (Vero cells) were cultured in 25-$cm^2$ tissue culture flasks (Greiner Bio-One) containing 10 ml of DulbeccModified Eagle's Medium supplemented with 10% heat-inactivated fetal calf serum, and incubated at 37° C. in a chamber with 5% CO2. After 4 days, monolayers were infected with $2\times10^6$ *T. cruzi* trypomastigotes (strain EP). Cultures were kept in the Dulbecco's Modified Eagle's Medium supplemented with 1% fetal calf serum plus glucose (10 mM) for 6 days after which trypomastigotes were harvested from the supernatant and separated from the remaining Vero cells by centrifugation at 600 g for 10 min, and later washed with PBS plus glucose (10 mM). Trypomastigotes were used to perform CML assays. Epimastigotes cultured in a liver infusion tryptone medium were harvested in the exponential phase of growth and then washed twice by centrifugation at 1,500 g for 15 min at 5° C., and by resuspending pellets in PBS (pH 7.2) to be then transferred to IIF slide wells at a dilution to obtain 20 parasites/field at 40×. The slides were allowed to dry for 12 h at RT, and later incubated for 1 h at 37° C. in a humidified chamber with 5 μl/well of serial dilutions (up to 1:800) of the study sera. After this period, the slides ere washed 3 times for 5 min by immersion in PBS (pH 7.2). After removing the excess buffer, wells were then incubated for 1 h with 5 μl of a 1:50 dilution of anti-human IgG FITC-conjugated serum (Sigma) plus 0.01% of Evan's blue in a humidified dark chamber. The excess of the conjugated serum was removed by rinsing the slides 3 times for 5 min in PBS. Slides were then observed under a trinocular epifluorescence microscope (Olympus Bh2) at 40×. A 'positive' result was considered to be the detection of fluorescence in the dilutions of sera higher than 1:60.

Human serum complement was obtained from healthy volunteers' blood (Laboratorio de Enzimologia de ParAsitos' staff). After allowing this blood to coagulate, sera was recovered by centrifugation at 500 g for 15 min at 4° C., and stored at −80° C. in aliquots. $5\times10^6$ trypomastigotes/ml were incubated with human serum complement at 37° C. for 30 min and then counted in a hemocytometer to determine lysis resistance in the absence of immune serum. Forty μl of trypomastigote suspension was mixed with 40 μl of the study sera (including samples of serum from healthy patients as well as a positive control) diluted 2, 4 and 8 times, and incubated at 37° C. for 30 min with constant shaking. Later, the tubes were placed on ice and parasites were then counted in a hemocytometer (only moving trypomastigotes) to determine the lysis percentage. It was considered a "positive" result when the lysis percentage was higher than 25% when using the highest sera dilution.

Results

In this present study, after administration of the oral suspension of Amiodarone and Itraconazole, the Cmax (maximum plasma levels) of Itravonazole is 13.5+/−8.5 μg/mL when given 10 mg/kg once daily. When Itraconazole is given at 5 mg/kg once daily, the Cmax of Itraconazole is 3.55+/−2.81 μg/mL. Previous study has shown that Itraconazole Cmax increase 5-6 fold with the increase from 5 mg/kg to 10 mg/kg once daily. (Dawn Merton, *Small Animal Clinical Pharmacology Therapeutics*, second edition Boothe, p 382)

Potential hepatotoxicity related to Amiodarone therapy is often a concern when deciding whether to initiate or continue treatment with this medication. Hepatotoxicity is mostly associated with long-term oral administration of the drug. Treating Chagas disease at its chronicle stage requires prolonged oral administration of the drug. Therefore, reducing hepatic side effect of the drug is critical to the treatment of the chagas disease.

Lower dose Amiodarone may reduce hepatic effects. Multiple blood chemistries in both dogs and monkeys displaying 0 hepatic effects and 0 arrythmias on the amiodarone, liver biopsies also showing no negative effects from amio/itra. Again efficacy was upheld by reducing parasitemia and cure rates.

Itraconazole is better absorbed orally when it is taken with a fatty meal or acidic drink (e.g. orange juice). Itraconazole plasma level is higher when given with food compared with when given the drugs without food. (Mol Pharm. 2013 Nov. 4; 10(11):4016-23. doi: 10.1021/mp4003249. Epub 2013 Aug. 29)

The present study provides a few advantages when compared with the current available treatments. In the present study, the dose of Itraconazole in the present invention is at about 10 mg/kg once daily, which results in more than 5-6 fold increase in plasma Itraconazole level as compared with the Cmax level of Itraconazole used a previous study (Paniz-Mondolfi et al., *Chemotherapy* 2009). In addition, in the present study, the formulation is taken with food. As shown in the results, Itraconazole plasma level is higher when it is taken with a meal. The higher plasma Itraconazole level kills the organism causing Chagas disease more rapidly. Additionally, the inventors provide that lower dose of Amiodarone of the present study at about 7.5 mg/kg can offset its hepatic side effects. Potential hepatotoxicity related to Amiodarone therapy is often a concern when deciding whether to initiate or continue treatment with this medication (Babatin et al., *Curr. Vasc. Pharmacol.* 2008).

Accordingly, the composition of the present invention is more effective and safer as compared to previous study (Paniz-Mondolfi et al., *Chemotherapy* 2009). Further, the once daily treatment regimen simplifies dosing for patients and increases compliance of taking the necessary doses by providing patients a simple to follow formula. Moreover, the flavored oral suspension decreases bitterness of medication, give a better mouth feel and cravability for patients to increase compliance. Compliance is important because the medicine will be taken in a long period of time (>6 months) to treat Chagas disease.

Example 2

I. Non Human Primate Study:

A treatment in accordance with the present disclosure was tested using 12 monkeys, namely 9 animals having Chagas disease that were treated with the pharmaceutical composition of the present disclosure, two diseased monkeys that were treated with a control, and one monkey that did not have the disease that was also treated with the control.

In these tests, therapeutic drug levels of Itraconazole were attempted using an increased dose of itraconazole at 50 mg/kg. Amiodarone maintained at 7.5 mg/kg. After 18 months of treatment, the animals' heart and intestinal tissues were examined histologically and through molecular analysis (PCR). Half the treatment group was found to have no lesions or organisms present. The other half of the treatment group had a very mild infiltrate of lymphocytes, plasma cells and some tested positive (3) for *T. cruzi* (chagas disease) in the tissue only. Peripheral PCR molecular analysis of whole blood was found to be negative for the organism for 6 months prior to discontinuation of the treatment. As indicated above, while the treatment was successful, this appeared to indicate that it was necessary to increase bioavailability of itraconazole through micronization/milling techniques as well as aim to reduce manufacturing costs. Accordingly, prior to additional testing, a dosage of Itraconazole and Amiodarone was prepared in accordance with the above example, but with nanomilling of the Itraconazole before formulating into pharmaceutical compositions and administration to patients. In this example, a suspension of itraconazole was prepared and then subject to milling using a media mill such as disclosed in Kumar et al., *J. Pharm. Sci.* 104:3018-3028 (2015), wherein Itraconazole (1%, w/v) was suspended in a desired concentration of an aqueous stabilizer solution, and the prepared suspension was stirred for 30 minutes or more for complete wetting of the drug by the stabilizer solution. The suspension (e.g., 150 mL) was then wet milled or wet grinded using a conventional wet milling or grinding device, namely one manufactured by Netzsch of Exton, Pa. Using this equipment, the mill is operated at a suitable speed, e.g., 2500 rpm in a continuous mode for a time suitable to reduce particle size to a range of 1 and 400 nm, e.g., 75 minutes. The temperature of the sample was maintained at below 25° C. during the process, and two cooling bath recirculators were used, including one attached to the milling device and the other attached to suspension recirculation chambers. During the milling process, the Itraconazole molecule is reduced to a particle size of 1 to 400 nm, e.g., 240-280 nm, or 260 nm, and then spray dried onto a sugar molecule (lactose or mannitol) before being combined with Amiodarone to form the pharmaceutical composition in accordance with the present disclosure.

After the milling process, the nano- and microcrystalline suspensions of itraconazole are spray dried onto a suitable substrate, which in this case was a sugar molecule (e.g., lactose or mannitol), using a conventional spray drying apparatus known as the B-290 spray drier manufactured by Buchi Labortechnik AG of Flawil, Switzerland. In the spray drying process, the drier is set at a temperature of 75° C. for the outlet and 110° C. for the inlet. The spray drying onto lactose or mannitol was useful in preventing against nanocrystal aggregation. As indicated above, the spray-dried powders resulting from this process produced Itraconazole at a reduced particle size of from about 1-400 nm. The use of the nanomilling techniques discussed above allowed for the increase of bioavailability of itraconazole by 2000% based on the reduction of Itraconazole particle size to about 1 to 400 nm. This allows the use of ¹⁄₂₀ of the drug that would normally be used in manufacturing and will save our target population a significant amount of expense.

II. Canine Study (Military Working Dog and Private Dogs)

Following the study above, a military working dog study was conducted and resulted in a determination that nanomilled Itraconazole combined with Amiodarone was effective at clearing *T. cruzi* from the body. This was confirmed this with molecular testing (PCR and Lytic antibodies). In these studies, therapeutic drug levels were readily obtained and generally fell between 5-10 mg/kg of itraconazole once daily combined with 7.5 mg/kg amiodarone once daily. In the initial dog study, 15 dogs were monitored that were on the medication after 12 months, and it showed that the micronized Itraconazole in combination with Amiodarone was successful in maintaining therapeutic drug levels can clearing the organism. Furthermore, these dogs had no worsening of symptoms and most importantly did not exhibit the fatal arrythmias that chronic Chagas disease is known for in the canine population. Typical parameters were measured (echocardiography, ECG, troponin, chemistry, Thyroid, CBC, and itraconazole levels). Derangements included ALT increases, skin eruptions, anorexia, vomiting. These were all dose related and responded quickly to reductions in itraconazole dosing, to achieve therapeutic drug levels. Subsequently, Subsequently, over 100 additional dogs were studied with elimination of *T. cruzi* in about 85 to 90% of the cases.

REFERENCES

Throughout this document, various references are mentioned. All such references are incorporated herein by reference, including the references set forth in the following list:

A. E. Paniz-Mondolfi, A. M. Perez-Alvarez, G. Lanza, E. Marquez, J. L. Concepcion, Amiodarone and Itraconazole, A rational therapeutic approach for the treatment of chronic Chagas' disease, *Chemotherapy* 2009; 55:228-233)

Babatin M, Lee S S, Pollak P T., Amiodarone Hepatotoxicity, Curr. Vasc. Pharmacol. 2008 July; 6(3):228-36

Gascfin J, Albajar P, Cafias E, et al: Diagnosis, management, and treatment of chronic Chagas' heart disease in areas where *Trypanosoma cruzi* infection is not endemic (in Spanish). Rev Esp Cardiol 2007; 60: 285-293.

Punukollu G, Gowda R M, Khan I A, et al: Clinical aspects of the Chagas' heart disease. Int J Cardiol 2007; 115: 279-283.

Urbina J A, Docampo R: Specific chemotherapy of Chagas disease: controversies and advances. Trends Parasitol 2003; 19: 495-501.

Coura J R, de Castro S L: A critical review on Chagas' disease chemotherapy. Mem Inst Oswaldo Cruz 2002; 97: 3-24.

Docampo R: Recent developments in the chemotherapy of Chagas' disease. Curr Pharm Des 2001: 1157-1164.

Urbina J A: New chemotherapeutic approaches for the treatment of Chagas' disease (American trypanosomiasis). Expert Opin Ther Pat 2003; 13: 661-669.

McCabe R E, Remington J S, Araujo F G: In vitro and in vivo effects of itraconazole against *Trypanosoma cruzi*. Am J Trop Med Hyg 1986; 35: 280-284.

Apt W, Aguilera X, Arribada A, et al: Treatment of chronic Chagas' disease with itraconazole and allopurinol. Am J Trop Med Hyg 1998; 59: 133-138.

Apt W, Arribada A, Zulantai I, et al: Itraconazole or allopurinol in the treatment of chronic American trypanosomiasis: the results of clinical and parasitological examinations 11 years post-treatment. Ann Trop Med Parasitol 2005; 99: 733-741.

Benaim G, Sanders J M, Garcia-Marchin Y, et al: Amiodarone has intrinsic anti-*Trypanosoma cruzi* activity and acts synergistically with posaconazole. J Med Chem 2006; 49: 892-899.

Krajewska-Kulak E, Niczyporuk W: Effects of the combination of ketoconazole and calcium channel antagonists against *Candida albicans* in vitro. Arzneimittelforschung 1993; 43: 782-783.

Moebius F F, Reiter R J, Bermoser K, et al: Pharmacological analysis of sterol delta8-delta7 isomerase proteins with [3H]ifenpro-dil. Mol Pharmacol 1998; 54: 591-598.

Urbina J A, Vivas J, Lazardi K, et al: Antiproliferative effects of delta 24(25) sterol methyl transferase inhibitors on *Tripanosoma* (Schyzotrypanum) *cruzi*: in vitro and in vivo studies. Chemotherapy 1996; 42: 294-307.

Urbina J A: Chemotherapy of Chagas' disease. Curr Pharm Des 2002; 8: 287-295.

Urbina J A: Specific treatment of Chagas' disease: current status and new developments. Curr Opin Infect Dis 2001; 14: 733-741.

Molina J, Martins-Filho O, Brenner Z, et al: Activities of the triazole derivative SCH 56592 (Posaconazole) against drug resistant strains of the protozoan parasite *Trypanosoma* (Schizotrypanum) *cruzi* in immunocompetent and immunodepressed murine hosts. Antimicrob Agents Chemother 2000; 44: 150-155.

Urbina J A, Payares G, Contreras L M, et al: Antiproliferative effects and mechanism of action of SCH 56592 against *Trypanosoma* (Schizotrypanum) *cruzi*: in vitro and in vivo studies. Antimicrob Agents Chemother 1998; 42: 1771-1777.

Krautz G M, Kissinger J C, Krettli A U: The targets of the lytic antibody response against *Trypanosoma cruzi*. Parasitol Today 2000; 16: 31-34.

Krautz G M, Galvao L M C, Cançado J R, et al: Use of a 24-kilodalton *Trypanosoma cruzi* recombinant protein to monitor cure of human Chagas' disease. J Clin Microbiol 1995; 33: 2086-2090.

Krettli A U, Brener Z: Resistance against *Trypanosoma cruzi* associated to anti-living trypomastigotes antibodies. J Immunol 1982; 128: 2009-2012.

Krettli A U, Cancado J R, Brener Z: Effect of specific chemotherapy on the levels of lytic antibodies in Chagas' disease. Trans R Soc Trop Med Hyg 1982; 76: 334-340.

Taibi A, Plumas-Marty B, Guevara-Espinoza A, et al: *Trypanosoma cruzi*: immunity induced in mice and rats by trypomastigote excretory-secretory antigens and identification of a peptide sequence containing a T cell epitope with protective activity. J Immunol 1993; 151: 2676-2689.

Singh B N: Amiodarone: a multifaceted anti-arrhythmic drug. Curr Cardiol Rep 2006; 8: 349-355.

Kumar S et al.: In Vitro and In Vivo Performance of Different Sized Spray-Dried Crystalline Itraconazole. J. Pharm Sci. 2015; 104:3018-3028.

What is claimed is:

1. A method of treating Chagas disease in a subject in need thereof, comprising: orally administering to the subject an effective amount of a pharmaceutical composition comprising:
   (a) a dose of Itraconazole wherein the dose of Itraconazole is in the range of about 7.5 mg/kg to about 12.5 mg/kg of a subject, and
   (b) a dose of Amiodarone wherein the dose of Amiodarone is in the range of about 6.5 mg/kg to about 8.5 mg/kg of a subject;
   and a pharmaceutically acceptable carrier.

2. The method of claim 1, wherein the subject is a mammal.

3. The method of claim 2, wherein the subject is selected from the group consisting of a human, a dog and a monkey.

4. The method of claim 1, wherein the pharmaceutical composition is administered once daily.

5. The method of claim 1, wherein the pharmaceutical composition is taken in conjunction with a meal.

6. A method of treating Chagas disease in a subject in need thereof, comprising: orally administering to the subject:

(a) a dose of Itraconazole wherein the dose of Itraconazole is in the range of about 7.5 mg/kg to about 12.5 mg/kg, and (b) a dose of Amiodarone wherein the dose of Amiodarone is in the range of about 6.5 mg/kg to about 8.5 mg/kg, wherein the Itraconazole and Amiodarone are administered in the form of a pharmaceutical composition; and wherein the pharmaceutical composition is in a form selected from the group consisting of a suspension, a tablet, a capsule, a caplet, a solution, a syrup, a dry product, and a controlled release product.

7. The method of claim 6 wherein the Itraconazole and Amiodarone are administered together in the form of a pharmaceutical composition.

8. The method of claim 6 wherein the Itraconazole and Amiodarone are administered separately.

9. The method of claim 6, wherein the Itraconazole and Amiodarone are administered once daily.

10. The method of claim 6 wherein the Itraconazole and Amiodarone are administered with food.

11. The method of claim 1 wherein the dose of Itraconazole is about 10 mg/kg of a subject and the dose of Amiodarone is about 7.5 mg/kg of a subject.

12. The method of claim 6 wherein the dose of Itraconazole is about 10 mg/kg of a subject and the dose of Amiodarone is about 7.5 mg/kg of a subject.

* * * * *